US011357705B2

United States Patent
Tignanelli et al.

(10) Patent No.: US 11,357,705 B2
(45) Date of Patent: Jun. 14, 2022

(54) PORTABLE, REUSABLE DISPENSING ASSEMBLY HAVING MULTIPLE OPERATING MODES

(71) Applicant: TW3 Properties LLC, Clinton Township, MI (US)

(72) Inventors: Jason S. Tignanelli, Oakland Township, MI (US); Matthew K. Winget, Oakland Township, MI (US); David R. Syrowik, Novi, MI (US)

(73) Assignee: TW3 PROPERTIES LLC, Clinton Township, MI (US)

( * ) Notice: Subject to any disclaimer, the term of this patent is extended or adjusted under 35 U.S.C. 154(b) by 420 days.

(21) Appl. No.: 16/710,034

(22) Filed: Dec. 11, 2019

(65) Prior Publication Data

US 2021/0177703 A1   Jun. 17, 2021

(51) Int. Cl.
| | |
|---|---|
| *A61J 7/04* | (2006.01) |
| *G01R 33/07* | (2006.01) |
| *A61J 7/00* | (2006.01) |
| *B65D 83/04* | (2006.01) |
| *A61J 1/03* | (2006.01) |

(52) U.S. Cl.
CPC ............ *A61J 7/0436* (2015.05); *A61J 1/035* (2013.01); *A61J 7/0084* (2013.01); *B65D 83/0472* (2013.01); *G01R 33/072* (2013.01)

(58) Field of Classification Search
CPC .. B65D 83/0472; B65D 83/0463; A61J 1/035; A61M 15/0045
USPC ..................... 221/30, 32, 265, 263
See application file for complete search history.

(56) References Cited

U.S. PATENT DOCUMENTS

| | | | |
|---|---|---|---|
| 3,224,634 A | | 12/1965 | Semsch |
| 4,274,550 A | * | 6/1981 | Feldstein ........... B65D 83/0472 |
| | | | 225/16 |
| 4,523,694 A | | 6/1985 | Veltri |
| 4,991,739 A | * | 2/1991 | Levasseur ............... G07F 11/24 |
| | | | 221/266 |
| 5,259,532 A | | 11/1993 | Schwarzli |
| 5,412,372 A | | 5/1995 | Parkhurst et al. |
| 5,582,323 A | | 12/1996 | Kurtenbach |
| 6,131,765 A | | 10/2000 | Barry et al. |
| 6,155,454 A | | 12/2000 | George et al. |
| 6,194,995 B1 | | 2/2001 | Gates |
| 6,259,654 B1 | | 7/2001 | de la Huerga |

(Continued)

OTHER PUBLICATIONS

United States Patent and Trademark Office, Non-Final Office Action for U.S. Appl. No. 16/710,056 dated May 3, 2022.

*Primary Examiner* — Timothy R Waggoner
(74) *Attorney, Agent, or Firm* — Brooks Kushman P.C.

(57) ABSTRACT

A portable, reusable dispensing assembly having multiple operating modes is provided. The assembly includes a housing having a compartment which is refillable with an elongated medication strip having a plurality of dosage form packages spaced apart along a longitudinal axis of the strip. A bi-directional, electromechanical actuator advances a first end of the strip from the compartment to a dose-ready area in the housing in a dispensing mode of the assembly and loads the strip into the compartment in a loading mode of the assembly. An actuator controller is configured to receive power and direction command signals to controllably supply DC power of a desired polarity to the actuator to control the operating mode of the assembly.

12 Claims, 4 Drawing Sheets

(56) References Cited

U.S. PATENT DOCUMENTS

| | | | |
|---|---|---|---|
| 6,394,306 B1 * | 5/2002 | Pawlo | B65D 83/0463 221/258 |
| 6,527,138 B2 | 3/2003 | Pawlo et al. | |
| 6,581,797 B2 | 6/2003 | McKinney, Jr. et al. | |
| 6,594,549 B2 | 7/2003 | Siegel | |
| 7,128,240 B1 | 10/2006 | Oesch | |
| 7,147,130 B1 | 12/2006 | Clark et al. | |
| 7,213,721 B2 | 5/2007 | Abdulhay et al. | |
| 7,359,765 B2 | 4/2008 | Varvarelis et al. | |
| 7,513,391 B2 | 4/2009 | Nakanishi | |
| 7,545,257 B2 | 6/2009 | Brue | |
| 7,735,683 B2 | 6/2010 | Handfield et al. | |
| 7,877,268 B2 | 1/2011 | Kulkarni | |
| 7,896,192 B2 | 3/2011 | Conley et al. | |
| 8,423,181 B2 | 4/2013 | Hallin | |
| 8,752,728 B2 | 6/2014 | Tignanelli et al. | |
| 9,326,558 B2 | 5/2016 | Martins et al. | |
| 9,351,907 B2 | 5/2016 | Luoma et al. | |
| 9,483,621 B2 | 11/2016 | Conley et al. | |
| 11,069,433 B2 | 7/2021 | Luoma et al. | |
| 2005/0154491 A1 | 7/2005 | Anderson et al. | |
| 2009/0315702 A1 | 12/2009 | Cohen Alloro et al. | |
| 2010/0123429 A1 | 5/2010 | Chen et al. | |
| 2011/0306852 A1 | 12/2011 | Hafezi et al. | |
| 2012/0312714 A1 * | 12/2012 | Luciano | B65D 83/0445 206/534 |
| 2013/0066463 A1 | 3/2013 | Luoma et al. | |
| 2014/0158703 A1 * | 6/2014 | Niinisto | G07F 11/42 221/253 |
| 2014/0346184 A1 | 11/2014 | Bae et al. | |
| 2015/0148943 A1 * | 5/2015 | Sullivan | A61J 7/0076 700/231 |
| 2016/0070075 A1 * | 3/2016 | Tsujita | G02B 6/4214 385/92 |
| 2019/0076333 A1 * | 3/2019 | Moore | G07F 11/005 |
| 2021/0401673 A1 * | 12/2021 | Feng | G16H 40/63 |

\* cited by examiner

PORTABLE, REUSABLE DISPENSING ASSEMBLY HAVING MULTIPLE OPERATING MODES

TECHNICAL FIELD

This invention relates in general to the field of portable, dispensing and, in particular, to portable, dispensing assemblies which are reusable and which have multiple operating modes.

Overview

A slide show entitled "Overcoming Barriers to Medication Adherence for Chronic Diseases" was published by the Center for Disease Control (CDC) on Feb. 21, 2017 and includes the following information:

1. For every 100 prescriptions written, 50-70 were filled by a pharmacy, 48-66 were picked up from the pharmacy, 25-30 were taken properly, 15-20 were refilled as prescribed and, at any given time, approximately 50% of patients were non-adherent.

2. Medication Adherence is a process by which patients take their medication as prescribed. One form of non-adherence is related to dosing history (i.e. the patient delays, omits or takes extra doses). Another form of non-adherence is related to time to event (i.e. patient discontinues the medication).

3. Medication Non-Adherence is a serious healthcare problem. Medication non-adherence in the United States costs anywhere between $100 billion to $300 billion per year; 33% to 69% of hospital admissions are due to non-adherence; and good adherence reduces adverse events and mortality.

4. Non-adherence is multi-factorial including socioeconomic factors, health care system factors and medical condition-related disease factors. For example, lower social economic status is associated with lower adherence; term-based care and post-hospital follow-up improve adherence; and concomitant conditions and comorbidities can impact adherence.

5. Other factors which impact adherence include therapy-related factors and patient related factors. Therapy-related factors include side effects of medications, number and different types of pills to be taken and complexity or changes to the regimen. Patient-related factors include: understanding of disease, its course and possible complications; expectations of improvement on medication; and perceptions of symptoms, either improving or worsening.

6. Medication adherence interventions can impact non-adherence. In evaluating the effect of intervention on adherence, medication adherence needs to be measured in valid, reliable and cost-effective ways to allow scale-up of interventions to wider clinical practice.

7. Intervention effects vary based on intervention type. For example, education and cognitive-focused intervention tend not to change patient behavior. Social support interventions are more likely to succeed in changing patient behavior. Multi-level and multi-faceted interventions which focus beyond healthcare providers are more likely to succeed in changing patient behavior.

8. Unintentional non-adherence can be at least partially overcome via medication packaging interventions such as pill boxes and blister packs. Also, integrating medication taking into existing patients' habits and routines can be helpful. For example, behavior prompts such as external reminders, phone alarms or medication logs can be helpful.

9. Among the patient, self-reported, intentional and unintentional reasons for non-adherence are the following in order of importance: forgot, ran out, away from home, trying to save money, bad side effects, was too busy, prescription wasn't working, didn't think prescription was needed and didn't like taking the prescription.

10. Among the types of interferences which improve cardiac medication adherence are frequent and regular reminder calls, both automated and non-automated, especially from pharmacists who were seen as supportive providers and caring people.

11. Also important in improving patient lives and medication adherence is social support from family and friends.

12. When a patient knows that medication adherence is being monitored, medication adherence appears to improve.

Solid oral dosage form drug products for human use include prescription drug products, over-the-counter drug products, biological drug products, and homeopathic drug products.

A "drug product" has been defined to mean a finished dosage form, e.g., a tablet or capsule that contains a drug substance, generally, but not necessarily, in association with one or more other ingredients.

A "solid oral dosage form" has been defined to mean capsules, tablets, or similar drug products intended for oral use.

Drug products in solid oral dosage form often times have distinct size, shape (i.e., round or oval) and color, which help to uniquely identify the drug product and the manufacturer or distributor of the product.

Oftentimes there are few, if any, controls limiting the amount of medication a user can remove from the mechanism bottle per each opening of the bottle. This results in intentional or accidental overdose, drug misuse and the illegal "selling" of prescription medications.

U.S. Published Application No. 2015/0148943 discloses a dispensing device for dispensing medications or other items required to be dispensed according to a predetermined schedule. A mechanism for advancing a bandolier containing the medications or other items to a dispensing position only when activated by an authorized user at predetermined time intervals is provided. Access to the bandolier is limited at all other times to personnel in a controlled facility. The dispensing device may be utilized to implement a method of controlling access to addictive prescription medications.

U.S. Pat. No. 6,594,549 discloses a medication dispensing system capable of connecting to the Internet. The medication dispensing system can be in the form of a periphery device having electronic means for linkage to a personal computer, PDA, cell phone or WEB TV or can be a stand-alone, on-site terminal having means to connect to the Internet. The medication dispensing system comprises a rotatable medication tray having a plurality of compartments, a servo-mechanism operatively connected to the medication dispensing tray, a microprocessor-based controller electronically connected to the servo-mechanism and being programmable to rotate the dispensing tray at a pre-set time. The controller also comprises a data store for maintaining and transmitting a variety of patient information, including the patient's medication regimen and compliance schedule. When connected to the Internet, the medication dispensing system transmits compliance and non-compliance notifications, allows the patient to order a refill medication or a new pre-filled dispensing tray, and provides the patient with healthcare news and databases.

U.S. Pat. No. 7,213,721 discloses a personal medication dispenser which has one or more chambers for holding a supply of pills. A feed mechanism is associated with each chamber and is selectively operative to dispense an incremental number of pills from each respective chamber. A programmable controller is coupled to control and operate the feed mechanism. The controller has a timer, a memory and an input means and is programmably operable by the user and/or by remote input from a smart card, PDA or various networks such as one having access to data from a pharmacy. The programming presets at least one of a time and a number of pills to be dispenses from each chamber. The controller operates an alarm to alert the user and operates the feed mechanism to dispense pills at the preset time and number, also detecting the user's access to obtain the dispensed pills.

U.S. Pat. No. 7,359,765 discloses an electronic pill dispenser including a container and a cap removably attached to the container. Components of the pill dispenser include a power source, pill dispenser circuitry, a real time clock, a counter, a display, a dispensing mechanism, a sensor, a visual indicator, an audible indicator, an input/output interface, an input output port, and a communication bus electrically interconnecting the components. The pill dispenser may also include a physical indicator, a locking mechanism, a transceiver, an antenna, and a modem.

U.S. Pat. No. 5,582,323 discloses a medication dispenser and monitor including a housing containing a plurality of pill dispensing compartments for dispensing medication to a patient at a desired time. The invention is programmed to dispense medication at the desired time and activates alarms if the proper procedure is not completed. The invention also contacts emergency personnel through phone lines and initiates two-way hands-free communication between the patient and the emergency personnel.

U.S. Pat. No. 8,752,728 discloses a portable, time-release, dosage form dispensing assembly. A hopper holds a supply of like, loose and randomly oriented dosage forms. The hopper including a bottom portion having an opening sized and shaped for receiving one of the dosage forms. An electromechanical apparatus dispenses the dosage forms from the hopper through the opening. The apparatus is adapted to dispense the dosage forms to a dispensing area one dosage form at a time. A programmable controller generates a set of control signals to control the apparatus to dispense a preselected number of dosage forms at a preselected time of day or time interval. A communication apparatus wirelessly communicates a first set of data to the controller to program the controller. The first set of data represents the preselected number and the preselected time of day or time interval.

Other related U.S. patent documents include U.S. Pat. Nos. 3,224,634; 4,523,694, 5,259,532; 5,412,372; 6,131,765, 6,155,454; 6,194,995; 6,259,654 6,581,797; 7,128,240; 7,147,130; 7,513,391; 7,545,257; 7,735,683; 7,877,268; 7,896,192; 8,423,181; 2009/0315702; 2010/0123429; and 2011/0306852.

As used herein, the term "sensor" is used to describe a circuit or assembly that includes a sensing element and other components. In particular, as used herein, the term "magnetic field sensor" is used to describe a circuit or assembly that includes a magnetic field sensing element and electronics coupled to the magnetic field sensing element.

As used herein, the term "magnetic field sensing element" is used to describe a variety of electronic elements that can sense a magnetic field. The magnetic field sensing elements can be, but are not limited to, Hall effect elements, magnetoresistance elements, or magnetotransistors. As is known, there are different types of Hall effect elements, for example, a planar Hall element, a vertical Hall element, and a circular vertical Hall (CVH) element. As is also known, there are different types of magnetoresistance elements, for example, a giant magnetoresistance element (AMR), a tunneling magnetoresistance (TMR) element, an Indium antimonide (InSb) sensor, and a magnetic tunnel junction (MTJ).

As is known, some of the above-described magnetic field sensing elements tend to have an axis of maximum sensitivity parallel to a substrate that supports the magnetic field sensing element, and others of the above-described magnetic field sensing elements tend to have an axis of maximum sensitivity perpendicular to a substrate that supports the magnetic field sensing element. In particular, planar Hall elements tend to have axes of sensitivity perpendicular to a substrate, while magnetoresistance elements and vertical Hall elements (including circular vertical Hall (CVH) sensing elements) tend to have axes of sensitivity parallel to a substrate.

Magnet field sensors are used in a variety of applications, including, but not limited to, an angle sensor that senses an angle of a direction of a magnetic field, a current sensor that senses a magnetic field generated by a current carried by a current-carrying conductor, a magnetic switch that senses the proximity of a ferromagnetic object, a rotation detector that senses passing ferromagnetic articles, for example, magnetic domains of a ring magnet, and a magnetic field sensor that senses a magnetic field density of a magnetic field.

In view of the above, there is an ongoing need for a portable, cost-effective medication dispensing assembly having multiple operating modes.

SUMMARY OF EXAMPLE EMBODIMENTS

An object of at least one embodiment of the present invention is to provide a portable, dispensing assembly which has multiple operating modes to improve medication adherence and which is reusable so that the assembly is cost-effective.

In carrying out the above object and other objects of at least one embodiment of the present invention, a portable, reusable dispensing assembly having multiple operating modes is provided. The assembly includes a housing having a compartment which is refillable with an elongated medication strip having a plurality of dosage form packages spaced apart along a longitudinal axis of the strip. A bi-directional, electromechanical actuator advances a first end of the strip from the compartment to a dose-ready area in the housing in a dispensing mode of the assembly and loads the strip into the compartment in a loading mode of the assembly. An actuator controller is configured to receive power and direction command signals to controllably supply DC power of a desired polarity to the actuator to control the operating mode of the assembly.

The actuator assembly may include a DC motor having a rotary output shaft and a drive gear coupled to the output shaft for driving the medication strip upon rotation of the drive gear by the DC motor.

The drive gear may be a sprocket wheel including sprockets to engage individual packages to advance the strip upon rotation of the wheel by the DC motor.

The actuator may include a non-contact position sensor to provide a position feedback signal as a function of the position of the medication strip. The controller may control the DC motor based on the position feedback signal.

The sensor may include at least one magnetic or ferromagnetic magnet mounted for movement with the drive gear and at least one magnetic field sensing element disposed adjacent and stationary with respect to the at least one magnet for sensing magnetic flux to produce the position feedback signal.

Each magnetic field sensing element may be a Hall effect sensor.

Further in carrying out the above object and other objects of at least one embodiment of the present invention, a portable, reusable dispensing assembly having multiple operating modes is provided. The assembly includes a housing having a compartment loaded with an elongated medication strip having a plurality of dosage form packages spaced apart along a longitudinal axis of the strip. A bi-directional, electromechanical actuator is coupled to the strip to advance a first end of the strip from the compartment to a dose-ready area in the housing in a dispensing mode of the assembly and to load the strip into the compartment in a loading mode of the assembly. An actuator controller is configured to receive power and direction command signals to controllably supply DC power of a desired polarity to the actuator to control the operating mode of the assembly.

The actuator may include a DC motor having a rotary output shaft and a drive gear coupled to the output shaft and to the strip to convert rotary motion of the output shaft to linear motion of the strip.

The drive gear may be a sprocket wheel including sprockets to engage individual packages to advance the strip upon rotation of the wheel by the DC motor.

The actuator may include a non-contact position sensor to provide a position feedback signal as a function of the position of the medication strip. The controller may control the DC motor based on the position feedback signal.

The sensor may include at least one magnetic or ferromagnetic magnet mounted for movement with the drive gear and at least one magnetic field sensing element disposed adjacent and stationary with respect to the at least one magnet for sensing magnetic flux to produce the position feedback signal.

Each magnetic field sensing element may be a Hall effect sensor.

DETAILED DESCRIPTION OF THE EXAMPLE EMBODIMENTS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
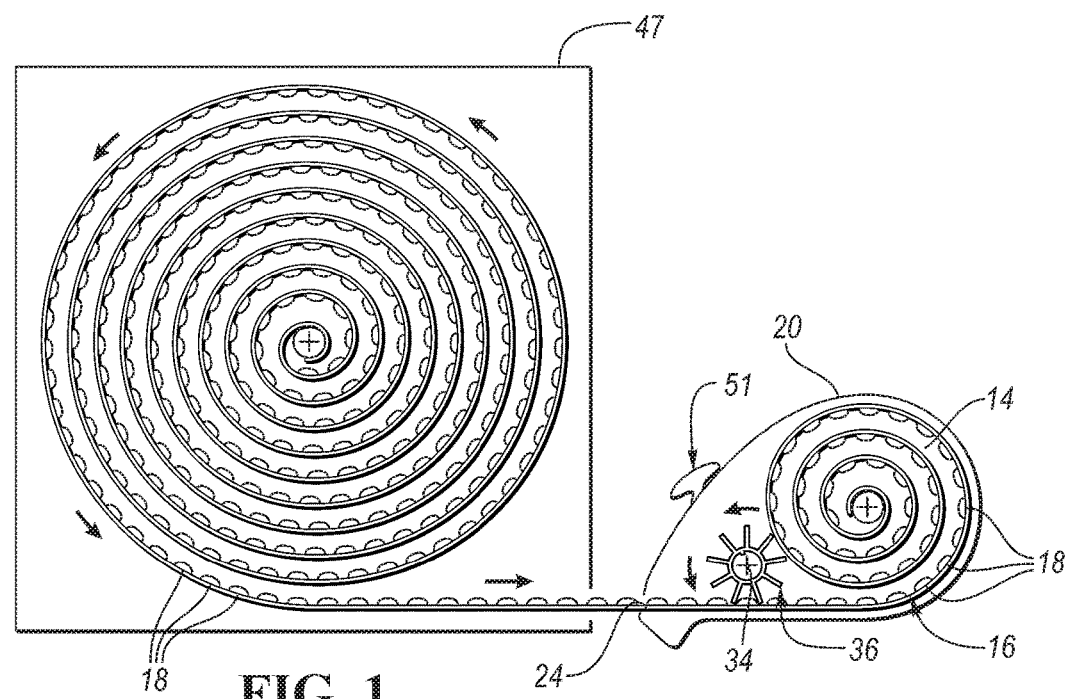
FIG. 1 is a schematic internal view illustrating the automated loading of a medication dispensing assembly with a medication strip in its loading operating mode, the assembly being constructed in accordance with at least one embodiment of the present invention.
Figure 2:
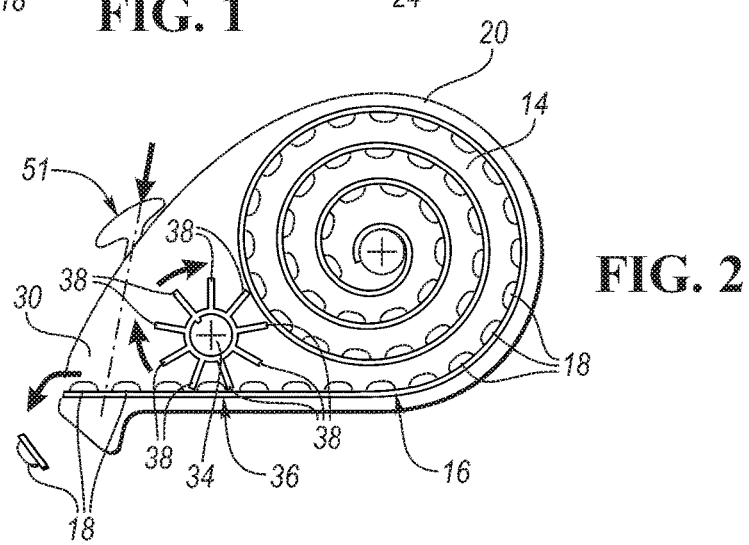
FIG. 2 is a side schematic internal view of the dispensing assembly of FIG. 1 in its dispensing mode.
Figure 3:
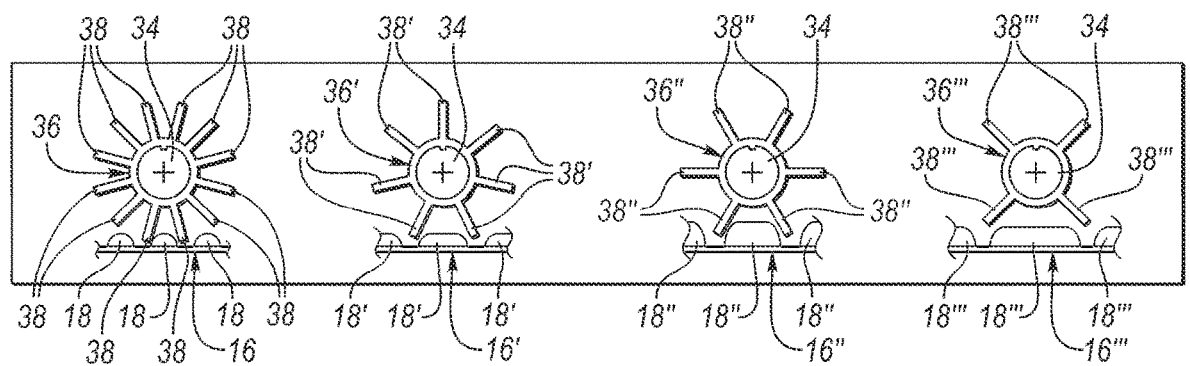
FIG. 3 is a side schematic view, partially broken away, of different-sized, interchangeable sprocket wheels for use in the assembly of FIGS. 1 and 2.
Figure 4:
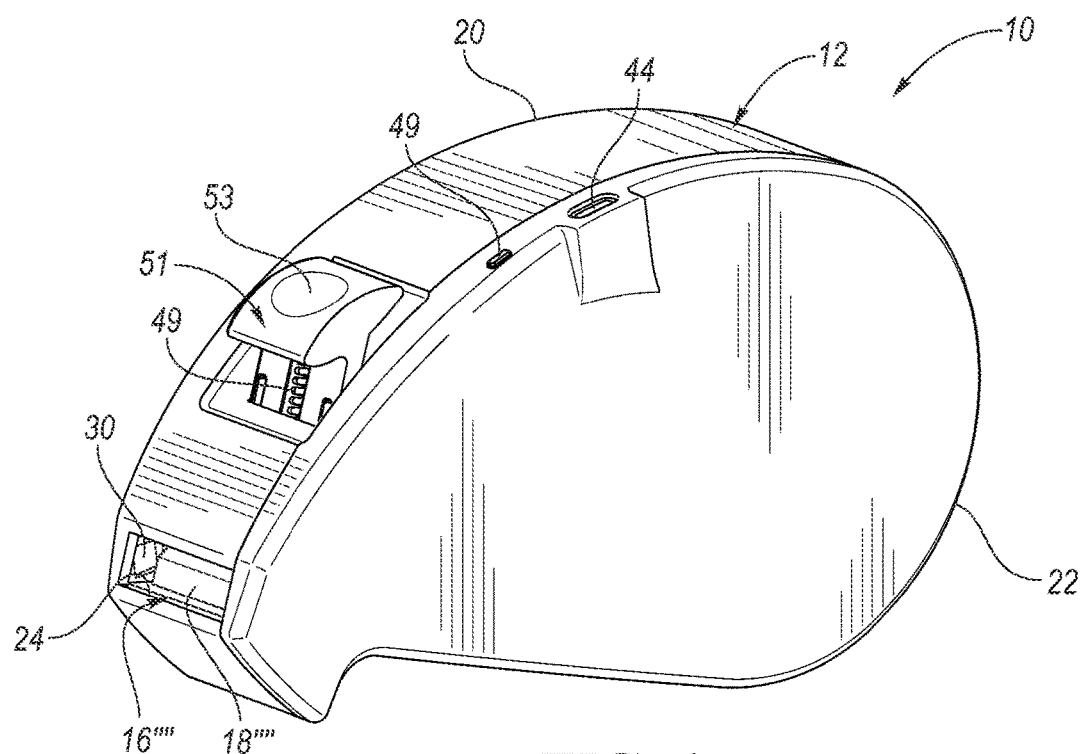
FIG. 4 is a perspective view of the medication dispensing assembly of FIGS. 1 and 2.

Referring now to drawing FIGS. 1, 2 and 4, a portable, time-release, dosage form dispensing assembly constructed in accordance with at least one embodiment of the present invention is generally indicated at 10. The assembly 10 includes a housing, generally indicated at 12, including a spiral-shaped compartment 14 that is refillable with an elongated, flexible, medication strip, generally indicated at 16, having a supply of dosage form packages 18 which contain dosage forms, such as tablets and/or capsules. The packages 18 are spaced apart along a longitudinal axis of the strip 16. Different embodiments of the strip are indicated at 16, 16', 16", 16''' and 16'''' at FIGS. 3 and 5. Similarly, different embodiments of the packages are indicated 18, 18', 18", 18''' and 18''''.

FIG. 1 shows the medication strip or blister pack 16 for use in the dispensing assembly 10 constructed in accordance with the principles of preferred embodiments of the invention. The strip 16 typically is made of a plastic individual packages or holders 18 for holding individual doses in the form of pills, tablets, or capsules. The packages 18 may be conventional clear plastic blisters insert-molded into the strip 16, or may consist of bubbles formed during molding of the strip 16. The strip 16 may also include indentations or detents (not shown) extending longitudinally along one or both sides of the strip 16, or perforations (not shown) on one or both sides of the strip 16. The size and spacing of the perforations and/or indentations depends on configuration of a sprocket wheel 36 used to advance the strip 16 and on the size of the individual packages 18. Arms or sprockets 38 of the sprocket wheel 36 are arranged to fit within or between the packages 18, to advance the strip 16 when the sprocket wheel 36 is rotated by a motor 32 as described hereinbelow.

The housing 12 includes a plastic main body part 20 and a removeable plastic cover 22 which is secured to the main body part 20 to form the housing 12. The main body part 20 has an opening 24 sized and shaped for receiving one end of the strip during loading of the strip 16 into the housing 12 during a loading mode of the assembly 10 as shown in FIG. 1 and to allow released dosage form packages 12 to be removed from the assembly 10 as shown in FIG. 2.

The assembly 10 also includes an electromechanical apparatus in the form of a bi-directional electromechanical actuator, generally indicated at 28, that dispenses or advances the dosage form packages 18 from the compartment 14 to a dose-ready area 30 in the housing 12 for subsequent removal of a released package through the opening 24. The apparatus 28 is adapted to dispense or advance the dosage form packages 18 to the dose-ready area 30 one dosage form package 18 at a time.

The electromechanical apparatus 28 includes an electric DC motor 32 having a rotary output shaft 34 and a drive gear in the form of a sprocket wheel 36 having sprockets 38 in driving engagement with the shaft 34. The motor 32 is supported within a hole 33 formed in a printed circuit (i.e. PC) board cover 35. Different embodiments of the wheel 36 and its sprockets 38 are shown in drawing FIGS. 3, 5 and 6, with the same reference number (36 and 38) but with single, double, triple and quadruple prime designations to indicate different sprocket wheels and their sprockets to handle different sized and shaped packages. The sprocket wheels of the figures are removably mounted on the shaft 34 to rotate therewith via a tongue and groove connection.

The wheel 36 is supported for rotary movement with the shaft 34 and the sprockets 38 of the wheel 36 drive the strip 16 by engaging the package 18 near the dose-ready area 30. As previously mentioned, the wheel 36 may be removable and replaced with a different-size wheel 36', 36", 36''' or 36'''' to enable the assembly 10 to advance and load different strips 16 having different sized packages 18 spaced apart at different sized lengths therein as shown in the drawing Figures.

Figure 7:
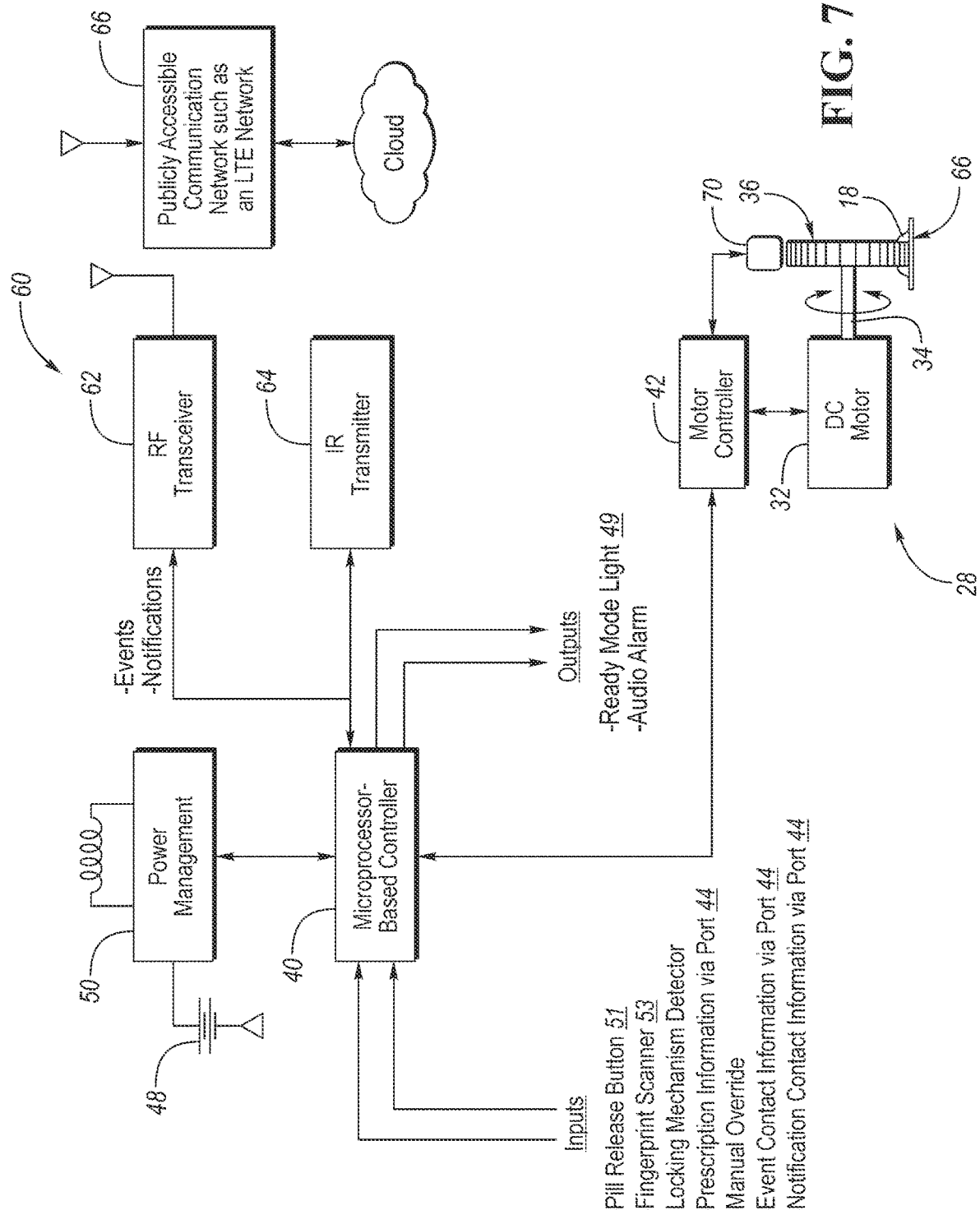
FIG. 7 is a schematic view of various electrical and electronic components of the assembly of FIGS. 1, 2, 4, 5 and 6 together with a bi-directional DC motor, its controller, a sprocket wheel driven by the motor and a feedback sensor.

The assembly 10 also includes a programmable, microprocessor-based controller 40 (FIG. 7) for generating and transmitting a set of power and direction command signals to an actuator controller 42 which controls the DC motor 32 to dispense a preselected number of dosage forms at a preselected time of day or time interval. Both the controller 40 and the controller 42 are mounted on the PC board 43. The controller 42, in turn, supplies DC power of a desired polarity to the motor 32 (which rotates in one direction or another) to control the operating mode of the assembly 10.

The assembly 10 further includes a communication port 44, for communicating contact and prescription data to the controller 40 to program the controller 40 via a cable 45. The cable 45 may also be used to supply electrical power to a rechargeable battery 48. The prescription data represents the preselected number and the preselected time of day or time interval that the strip 16 is to be advanced. The contact data allows the assembly 10 to wirelessly transmit event data via a publicly accessible network such as an LTE communications network 66 to a remote database on cloud storage and to wirelessly transmit event notification data to at least one of the patient, the pharmacist, a care giver and the patient's doctor.

Preferably, the blister pack or medication strip 16 is loaded into the dispensing assembly 10 at a pharmacy from a source or supply 47 of the strip 16. A portion of the strip 16 is driven into the assembly 10 upon rotation of the shaft 34 in one direction. The loaded assembly 10 is provided to a patient upon presentation by the patient of a verified prescription for the contents of the dispensing assembly 10. When a prescription and valid patient identification are presented to the pharmacist, the pharmacist enters the number of doses, dosage intervals, prescription expiration date, and any other information relevant to dispensing of the medications into the dispensing assembly 10. Alternatively, the data can be entered automatically via the cable 45. Contact information may be entered by the pharmacist through the port 44, a touch screen, or any other data entry means, with the patient being the only person that can access individual released packages 18 contained in the dispenser assembly 10. Pharmacists typically are the only persons that can input contact and prescription data or information, including the dosage and duration of the prescription.

When a programmed interval between doses has elapsed, an LCD or light 49 may display the availability of access, at which time the patient can enter a password or either press a button 51 and/or input biometric information through a fingerprint sensor 53 or the like contained in the button 51 or at another location on the housing 12, to cause the motor 32 to advance the strip 16 and enable removal of a dosage form package 18 after cutting of a free end section of the strip 16 by the manually-operated button. The button 51 moves a cutting blade 55 against the bias of a spring 49 to cut through the strip 16 upon depressing the button 51. The blade 55 cuts through the strip 16 until it engages an anvil 57 supported in the part 20. The anvil 57 is typically electronically connected to the controller 40 to indicate the release of a package 18.

A locking mechanism (not shown) may prevent removal of the cover 22 from the main body part 20 and prevent access to the housing 12 by a user of the assembly 10. The locking mechanism may be locked/unlocked by a key (not shown).

The assembly 10 may also include a door (not shown) having open and closed positions. The door may be movably connected to the main body part 20 to permit access to the released dosage form package in the dose-ready area 30 in the open position of the door.

A power management circuit or circuitry 50 is coupled to the battery 48 and receives an electrical power signal via the port 44 to recharge the battery 48. The battery 48 provides electrical energy to the controller 40, the electromechanical apparatus 28, communication apparatus 60 and the motor controller 42.

In one embodiment, the communication apparatus 60 includes a transceiver such as an RF (i.e., radio frequency) transceiver 62. The communication apparatus may also include an IR (i.e. infrared) transmitter 64 to wirelessly communicate a set of data from the controller 40. The plastic housing 10 is preferably "transparent" to the RF and infrared signals. A set of data which is stored and transmitted may represent the number of dispensed dosage forms which the microprocessor 40 keeps track of. The number of angular rotations of the shaft 34 is input to the microprocessor 40 (FIG. 5) typically via the controller 42.

In another embodiment, the two-way communication apparatus 60 includes circuitry including an electrical coil (not shown) to inductively receive the electrical power signal. The electrical coil may be embedded in the plastic housing 10.

The strip 16 may be driven by the sprocket wheel 36 that directly engages the dose holders or packages 18. A free end section of the strip 16 is cut away from the strip 16 as shown in FIG. 2 in order to remove a single one of the individual dose-containing holders or packages 18 when the strip 16 is advanced into the dose-ready area 30.

The DC motor 32 advances the strip 16 by a predetermined distance corresponding to the dispensing of a single dose package 18. A timer prevents advance of the motor 32 until a predetermined interval has elapsed after the last dispensation, after which the DC motor 32 may be caused to advance the strip 16 by one dose when the user presses the dispensing button 53 or the like. The sprocket wheel 36 may be directly driven by the DC motor as shown, or indirectly driven through additional gears or other transmission components. The packages 18 may exit the dispensing assembly via a chute or passage having multiple turns that limit access to the strip 16 from outside the dispensing assembly 10.

The DC motor 32 is preferably a stepper or servo motor, such as a brushless DC electric servo motor, which divides its rotation into a number of equal steps, enabling the precise advance of the strip 16 by a predetermined distance corresponding to one or more of the individual doses. The stepper motor's position can be commanded to move and hold at one of the steps, allowing for dispensing of exactly the prescribed number of doses or pills at one time. Motors other than stepper or servo-motors may carry out the same advance and hold function if properly controlled, but a stepper motor is preferred because it can be controlled to hold a fixed position against an external torque, thereby holding the strip 16 at the last dispensing position until advancement is permitted and preventing the strip 16 from being forcibly advanced to enable a user to access doses at other than the pre-programmed interval.

Figure 5:
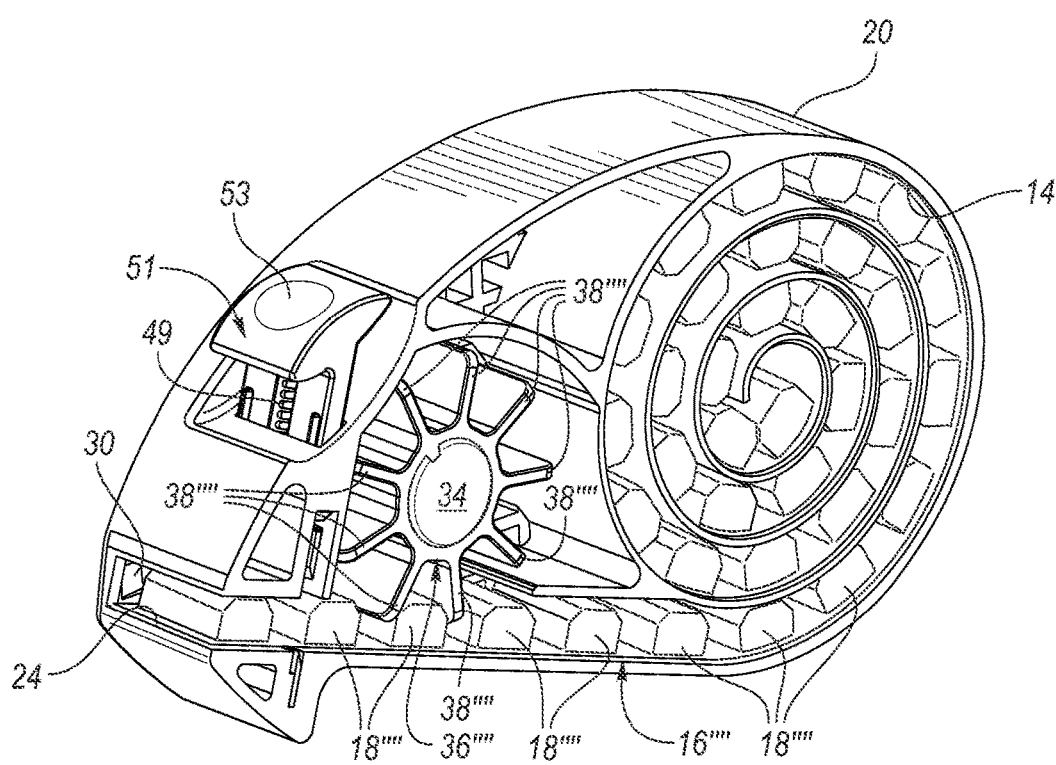
FIG. 5 is an internal view of the assembly of FIGS. 1, 2 and 4 which illustrates various components of the assembly.
Figure 6:
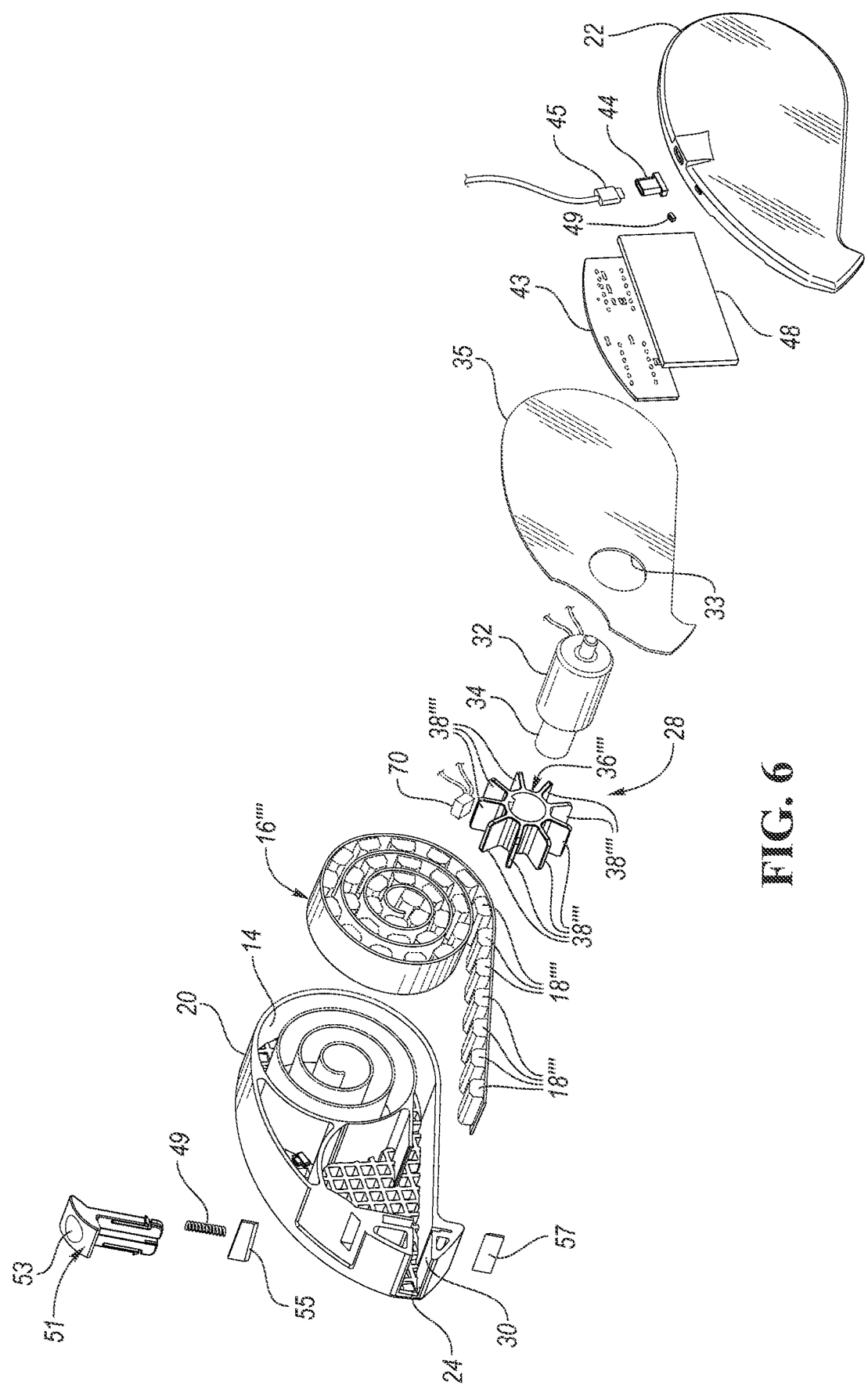
FIG. 6 is an exploded perspective view of the assembly of FIGS. 1, 2, 4 and 5.

FIG. 5 schematically illustrates the major electrical and electronic components of at least one embodiment of the assembly 10. The "brains" of the assembly 10 is the microprocessor 40 which composes and sends IR transmit data packets to the IR transmitter 64 and composes, sends and receives RF data packets via the RF transceiver 62. The microprocessor 40 may also be coupled to a detector or sensor (such as a proximity sensor (not shown)) to monitor the number of the dosage forms. The microprocessor 40 is also preferably coupled to switch(es) (such as monitor switches or motion switches) and/or electrical signals from drive circuitry of the various electromechanical parts of the assembly 10, the RF transceiver 62 and the IR transmitter 64. The microprocessor 40 may also display messages on an LED or LCD display (not shown) of the assembly 10, and/or may provide an audio alert via a sound transducer (not shown) of the assembly 10.

In one example embodiment, the medication strip 16 is electromechanically driven by the actuator assembly including a rotary actuator such as the DC servomotor or a DC stepper motor. The servomotor may be, for example, a brushed or brushless DC servomotor, the operation of which is controlled by a motor drive or driver (such as an H bridge motor driver) within the controller 42. The brushed or brushless motor 32 may have its rotary speed and position controlled by pulse width modulation (PWM) control so that the position of the medication strip 16 is adjusted.

The motor controller 42 outputs servomotor drive commands to the servomotor 32 based on outputs from a Hall effect sensor(s) 70, current feedback from the servomotor 32 and/or decoded commands from the microprocessor-based controller 40. The motor controller 42 controls the servomotor 32 through the motor drive of the motor controller 42 so that the linear position of the medication strip 16 is changed. In other words, the microprocessor 40 outputs servomotor drive commands to the motor controller 42 which controls the servomotor 32 and, the linear position of the medication strip 16.

A power source or circuit of the motor controller 42 supplies electric power of predetermined voltage levels to the servomotor 32 and the Hall effect sensor(s) 70 through the motor drive or driver. A transceiver within the motor controller 42 is a communication interface circuit connected to the microprocessor-based controller 40 for communications and operates as a receiver section for the motor controller 42 and a transmitter section back to the microprocessor-based controller 40. The motor driver typically includes a driver circuit for driving the servomotor 32.

The Hall effect sensor 70 is typically provided near or is coupled to the rotary output shaft 34 of the servomotor 32 or near or coupled to the sprocket wheel 36 (which mechanically couples the output shaft 34 of the motor 32 to the medication strip 16) and may be driven in synchronization with the rotation of the servomotor 32 to generate pulse signals which are received by the microprocessor-based controller 40.

The motor controller 42 typically includes a memory and may be configured as a conventional microcomputer including a CPU, a ROM, a RAM, and the like or as a hardwired logic circuit.

The microprocessor-based controller 40 and the motor controller 42 may perform data communications regularly. In such data communications, the motor controller 42 may transmit state data indicating the state of the servomotor 32 to the microprocessor-based controller 40. The state data may include a present rotation position of the servomotor 32, that is, count value of a rotation position counter stored in a memory of the motor controller 42.

The microprocessor-based controller 40 and/or the motor controller 42 may confirm the present rotation position of the servomotor 32. The microprocessor-based controller 40 then may set a target stop position of the servomotor 32 based on various states detected by non-contact position sensor commands and the present rotation position of the servomotor 32, and generates a servomotor drive command for driving the servomotor 32 to one or more target stop positions. Such a position sensor (i.e. sensor 70) provides a position feedback signal as a function of the position of the medication strip 16. The sensor 70 may include at least one magnetic or ferromagnetic magnet mounted for movement on the actuator assembly (i.e. one or more sprockets 38 of the sprocket wheel 36) and at least one magnetic field sensing element disposed adjacent and stationary with respect to the at least one magnet in the housing 12 for sensing magnetic flux to produce the position feedback signal. Each magnetic field sensing element is preferably the Hall effect sensor 70.

When the logic circuit of the motor controller 42 receives servomotor drive commands from the microprocessor-based controller 40 through its transceiver, it transmits drive commands or signals to the motor drive or driver to rotate the servomotor 32 in the forward or reverse direction so that the servomotor 32 stops at a desired target stop position.

If the detected, present rotary position of the servomotor 32 arrives at the target stop position, that is, the present position coincides with the target stop position, the logic circuit of the motor controller 42 transmits a stop command to the motor driver for stopping the servomotor 32.

Some advantages of at least one embodiment of the present invention include:

(1) Cost Savings—Will reduce costs for insurance companies paying over $100 billion per year for overdose-related claims. Will also limit litigations toward doctors, pharmacies, and pharmaceutical companies for substance abuse cases.

(2) Risk Management—Liabilities of doctors, pharmacies, and pharmaceutical companies will decrease, therefore giving them more comfort in successfully doing their jobs without fear of lawsuits, license revocation, or scrutiny due to patient abuse. This should also decrease their liability insurance cost.

(3) Public Safety—This invention promotes a safer, healthier population by reducing the illnesses, deaths, and psychological problems associated with drug abuse.

(4) Senior Citizen Comfort—Many senior citizens can provide for themselves without assistance from others. In many cases, seniors are fully capable of unassisted living, but have a high risk of accidental overdose by forgetting if they have taken their medication or not.

(5) Prescription Drug Black Market Impact—Without immediate access to multiple pills at a time, prescription drug trafficking should decrease.

(6) Hospitals—By lowering the number of overdose patients to the emergency room, doctors and nurses can put more focus on trauma, or ill patients.

The following are steps which are typically taken before, during and after use of the previously described medication dispensing assembly:

1) Prescription written
2) Assembly programmed at pharmacy per prescription
3) Assembly filled at pharmacy 4) Patient Fingerprint scanned and numeric code set at pharmacy and programmed to assembly (Assembly preferably will also be equipped with a manual override for up to 24 hours of dosage)

5) Assembly will be in "ready mode" for patient to press dosage form release button 6) Once first dose is taken, the timer will reset to countdown from prescribed dosage time 7) When in "ready mode," a light will blink and an alert will be sent to show the patient that next dose is ready to be taken. After one hour with no response, an alarm will sound and another alert will be sent. Timer will not reset countdown until patient releases or refuses that dose.

8) Events to be captured and stored (sent to cloud via LTE Communication network or similar network)
  1) fingerprints
  2) Dose ready times
  3) Dose taken times
  4) Dose missed
  5) Dose Refused
  6) Tampering with locking mechanism 9) Notifications to be sent (to doctors, patients, care givers, etc.)
  1) Dose ready (patient via smartphone)
  2) Dose missed reminder (patient/care giver via smartphone)
  3) Tampering with locking mechanism (doctor/pharmacist/caregiver)
  4) Assembly moving or traveling (patient/caregiver/pharmacist/doctor)
  5) Dose taken or refused vs. dose ready times—to show patterns and patient habits (doctor)

10) Once all doses are taken, assembly will alert as such and deactivate, patient can then return assembly to pharmacy in person, or by mail.

11) Pharmacy disassembles & cleans assembly, downloads data to server, and resets assembly.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A portable, reusable dispensing assembly having multiple operating modes, the assembly comprising:
  a housing including a compartment which is refillable with an elongated medication strip having a plurality of dosage form packages spaced apart along a longitudinal axis of the strip;
  a bi-directional, electromechanical actuator having first and second directions to advance a first end of the strip from the compartment to a dose-ready area in the housing in a dispensing mode of the assembly in the first direction and to load the strip from a source or supply of the strip by driving the strip into the compartment in an automated loading mode of the assembly in the second direction; and
  an actuator controller configured to receive power and direction command signals to controllably supply DC power of a desired polarity to the actuator to control the operating mode of the assembly.

2. The assembly as claimed in claim 1, wherein the actuator assembly includes a DC motor having a rotary output shaft and a drive gear coupled to the output shaft for driving the medication strip upon rotation of the drive gear by the DC motor.

3. The assembly as claimed in claim 2, wherein the drive gear is a sprocket wheel including sprockets to engage individual packages to advance the strip upon rotation of the wheel by the DC motor.

4. The assembly as claimed in claim 2, wherein the actuator includes a non-contact position sensor to provide a position feedback signal as a function of the position of the medication strip, the controller controlling the DC motor based on the position feedback signal.

5. The assembly as claimed in claim 4, wherein the sensor includes at least one magnetic or ferromagnetic magnet mounted for movement with the drive gear and at least one magnetic field sensing element disposed adjacent and stationary with respect to the at least one magnet for sensing magnetic flux to produce the position feedback signal.

6. The assembly as claimed in claim 5, wherein each magnetic field sensing element is a Hall effect sensor.

7. A portable, reusable dispensing assembly having multiple operating modes, the assembly comprising:
  a housing including a compartment loaded with an elongated medication strip having a plurality of dosage form packages spaced apart along a longitudinal axis of the strip;
  a bi-directional, electromechanical actuator having first and second directions coupled to the strip to advance a first end of the strip from the compartment to a dose-ready area in the housing in a dispensing mode of the assembly in the first direction and to load the strip from a source or supply of the strip by driving the strip into the compartment in an automated loading mode of the assembly in the second direction; and
  an actuator controller configured to receive power and direction command signals to controllably supply DC power of a desired polarity to the actuator to control the operating mode of the assembly.

8. The assembly as claimed in claim 7, wherein the actuator includes a DC motor having a rotary output shaft and a drive gear coupled to the output shaft and to the strip to convert rotary motion of the output shaft to linear motion of the strip.

9. The assembly as claimed in claim 8, wherein the drive gear is a sprocket wheel including sprockets to engage individual packages to advance the strip upon rotation of the wheel by the DC motor.

10. The assembly as claimed in claim 8, wherein the actuator includes a non-contact position sensor to provide a position feedback signal as a function of the position of the medication strip, the controller controlling the DC motor based on the position feedback signal.

11. The assembly as claimed in claim 10, wherein the sensor includes at least one magnetic or ferromagnetic magnet mounted for movement with the drive gear and at least one magnetic field sensing element disposed adjacent and stationary with respect to the at least one magnet for sensing magnetic flux to produce the position feedback signal.

12. The assembly as claimed in claim 11, wherein each magnetic field sensing element is a Hall effect sensor.

* * * * *